(12) United States Patent
Waizenegger et al.

(10) Patent No.: US 8,770,975 B2
(45) Date of Patent: Jul. 8, 2014

(54) METHOD OF MAKING A DENTAL RESTORATION FROM A FRAME AND A VENEER

(75) Inventors: Josef A. Waizenegger, Seefeld (DE); Till Meurer, Wörthsee (DE); Thomas B. Hiebel, Andechs/Erling (DE); Bastian P. Kirchner, Gilching (DE); Michael A. Kraemer, Landsberg am Lech (DE)

(73) Assignee: 3M Innovative Properties Company, St. Paul, MN (US)

( * ) Notice: Subject to any disclaimer, the term of this patent is extended or adjusted under 35 U.S.C. 154(b) by 371 days.

(21) Appl. No.: 13/139,692

(22) PCT Filed: Dec. 1, 2009

(86) PCT No.: PCT/US2009/066167
§ 371 (c)(1),
(2), (4) Date: Jun. 14, 2011

(87) PCT Pub. No.: WO2010/074890
PCT Pub. Date: Jul. 1, 2010

(65) Prior Publication Data
US 2011/0244429 A1    Oct. 6, 2011

(30) Foreign Application Priority Data
Dec. 15, 2008  (GB) .................................. 0822751.4

(51) Int. Cl.
*A61C 5/10*       (2006.01)
*A61C 13/08*      (2006.01)
*G06F 19/00*      (2011.01)
*A61C 13/00*      (2006.01)
*A61C 13/20*      (2006.01)

(52) U.S. Cl.
USPC .......... 433/223; 433/202.1; 433/204; 700/98; 700/188; 264/16; 264/17

(58) Field of Classification Search
USPC .......................... 700/97–98, 118, 163; 703/1; 264/16–20; 433/180, 191, 194, 201.1, 433/202.1, 204, 219, 223, 226
See application file for complete search history.

(56) References Cited

U.S. PATENT DOCUMENTS

| 4,431,420 A | 2/1984 | Adair |
| 4,433,959 A | 2/1984 | Faunce |

(Continued)

FOREIGN PATENT DOCUMENTS

| CA | 2630250 | 5/2007 |
| DE | 19944130 | 4/2001 |

(Continued)

OTHER PUBLICATIONS

Ebert, "Direct Inkjet Printing of Dental Prostheses Made of Zirconia", J. Dent. Res. 2009, vol. 88, No. 7, pp. 673-676.

(Continued)

*Primary Examiner* — Ramesh Patel
(74) *Attorney, Agent, or Firm* — X. Christina Huang (57) ABSTRACT

A method of making a dental restoration is provided. The dental restoration comprises a frame and a veneer. An inner veneer surface and an outer frame surface are adapted to be mated with one another to form the dental restoration. The method in particular comprises steps of (a) providing an outer veneer surface; (b) determining an outer frame surface, based on the outer veneer surface; (c) determining an inner veneer surface, based on the outer frame surface; and (d) providing an inner frame surface, based on a natural tooth surface. The method may be advantageous for rapid, precise and inexpensive manufacturing of a dental restoration.

11 Claims, 5 Drawing Sheets

(56) References Cited

U.S. PATENT DOCUMENTS

| | | | |
|---|---|---|---|
| 4,650,418 A | | 3/1987 | Blair |
| 4,773,859 A | * | 9/1988 | Obersat .................. 433/177 |
| 4,828,117 A | | 5/1989 | Panzera |
| 5,131,844 A | * | 7/1992 | Marinaccio et al. ........... 433/72 |
| 5,346,397 A | | 9/1994 | Braiman |
| 5,482,732 A | | 1/1996 | Kramer |
| 5,745,229 A | | 4/1998 | Jung |
| 5,902,441 A | | 5/1999 | Bredt |
| 6,106,747 A | * | 8/2000 | Wohlwend .................. 264/16 |
| 6,121,175 A | | 9/2000 | Drescher |
| 6,200,137 B1 | | 3/2001 | Holand |
| 6,306,784 B1 | | 10/2001 | Drescher |
| 6,322,728 B1 | | 11/2001 | Brodkin |
| 6,354,836 B1 | * | 3/2002 | Panzera et al. ............... 433/215 |
| 6,398,554 B1 | | 6/2002 | Perot |
| 6,955,776 B1 | | 10/2005 | Feenstra |
| 6,994,549 B2 | | 2/2006 | Brodkin |
| 7,086,863 B2 | | 8/2006 | Van der Zel |
| 7,452,836 B2 | | 11/2008 | Apel |
| 2002/0082316 A1 | | 6/2002 | Karmaker |
| 2002/0125592 A1 | | 9/2002 | Schulman |
| 2004/0185422 A1 | | 9/2004 | Orth |
| 2005/0023710 A1 | | 2/2005 | Brodkin |
| 2005/0127544 A1 | * | 6/2005 | Brodkin et al. ................ 264/16 |
| 2006/0082033 A1 | | 4/2006 | Hauptmann |
| 2006/0099552 A1 | * | 5/2006 | van der Zel et al. .......... 433/223 |
| 2006/0106484 A1 | | 5/2006 | Saliger |
| 2006/0111806 A1 | * | 5/2006 | Kraemer et al. .............. 700/117 |
| 2006/0257824 A1 | * | 11/2006 | Pfeiffer et al. ................. 433/218 |
| 2006/0261503 A1 | * | 11/2006 | Sago et al. .................... 264/16 |
| 2007/0077534 A1 | | 4/2007 | Saliger |
| 2007/0154868 A1 | | 7/2007 | Scharlack |
| 2007/0212667 A1 | * | 9/2007 | Jung et al. .................... 433/223 |
| 2008/0318189 A1 | | 12/2008 | Brodkin |
| 2009/0286206 A1 | * | 11/2009 | Braich .......................... 433/226 |
| 2010/0221682 A1 | * | 9/2010 | Burger et al. ............... 433/203.1 |
| 2010/0248189 A1 | * | 9/2010 | Burger et al. ............... 433/203.1 |
| 2011/0275031 A1 | * | 11/2011 | Jana et al. .................... 433/172 |

FOREIGN PATENT DOCUMENTS

| | | |
|---|---|---|
| DE | 60112245 | 3/2006 |
| DE | 102005034803 | 3/2006 |
| DE | 60020574 | 4/2006 |
| DE | 60023315 | 8/2006 |
| DE | 102006015014 | 10/2007 |
| EP | 431924 | 6/1991 |
| EP | 795311 | 9/1997 |
| EP | 1250895 | 10/2002 |
| EP | 1293174 | 3/2003 |
| EP | 1454596 | 9/2004 |
| EP | 1645663 | 4/2006 |
| EP | 1712534 | 10/2006 |
| EP | 1974688 | 10/2008 |
| EP | 1992302 | 11/2008 |
| EP | 2050417 | 4/2009 |
| EP | 2236121 | 10/2010 |
| WO | WO 94/19112 | 9/1994 |
| WO | WO 94/27517 | 12/1994 |
| WO | WO 03/066326 | 8/2003 |
| WO | WO 2004/073961 | 9/2004 |
| WO | WO 2006/120255 | 11/2006 |
| WO | WO 2007/028787 | 3/2007 |
| WO | WO 2007/060142 | 5/2007 |
| WO | WO 2008/009495 | 1/2008 |
| WO | WO 2008/103024 | 8/2008 |
| WO | WO 2008/144342 | 11/2008 |
| WO | WO 2009/052082 | 4/2009 |
| WO | WO 2009/070469 | 6/2009 |

OTHER PUBLICATIONS

Gbureck, "Preparation of Tricalcium Phosphate/calcium Pyrophosphate Structures Via Rapid Prototyping", J. Mater. Sci., Mater. Med., 2008, vol. 19, pp. 1559-1563.

Moon, "Ink-jet Printing of Binders for Ceramic Components", J. Am. Ceram. Soc., 2002, vol. 85, No. 4, pp. 755-762. ISSN 0002 7820.

Seitz, "Three-Dimensional Printing of Porous Ceramic Scaffolds for Bone Tissue Engineering", J. Biomed. Mater. Res. Part B: Appl. Biomater., 2005, vol. 74B, pp. 782-788.

Wang, "Solid Freeform Fabrication of Permanent Dental Restorations Via Slurry Micro-extrusion", J. Am. Ceram. Soc., 2006, vol. 89, No. 1, pp. 346-349.

European Search Report for PCT Application No. 07108206, 5 pgs.

Written Opinion for the ISA International Application No. PCT/US2008/063611, 9 pgs.

International Search Report for PCT/US2008/063611; 6 pgs.

International Search Report for PCT/US2008/079788, 6 pgs.

Written Opinion of the ISA for International Application No. PCT/US2008/079788, 10 pgs.

European Search Report for PCT Application No. 07118476, 10 pgs.

Search Report for GB App. No. GB0822751, 4 pgs.

Written Opinion of the ISA for International Application No. PCT/US2009/066167, 5 pgs.

International Search Report for PCT/US2009/066167, 4 pgs.

* cited by examiner

METHOD OF MAKING A DENTAL RESTORATION FROM A FRAME AND A VENEER

CROSS REFERENCE TO RELATED APPLICATIONS

This application is a national stage filing under 35 U.S.C. 371 of PCT/US2009/066167, filed Dec. 1, 2009, which claims priority to Great Britain Patent Application No. 0822751.4 filed Dec. 15, 2008, the disclosures of which are incorporated by reference in their entirety herein.

FIELD OF THE INVENTION

The invention is related to a method of making a dental restoration. In particular the invention concerns a method which includes computer aided design of the dental restoration. Further the invention is directed to a system providing for performing of such method, and which provides for manufacturing of the dental restoration.

BACKGROUND ART

Dental restorations or prostheses are often made as a configuration of two or more components, with the individual components providing different characteristics for the restoration. For example, a framework may provide good structural support, and a veneer may provide good aesthetics. The framework generally is a supporting structure for the dental restoration that provides mechanical stability and usually comprises an interface by which the restoration can be affixed to a prepared tooth of a patient. The veneer provides for pleasing aesthetic characteristics so that the restoration resembles a natural tooth in shape and appearance. In addition, both the frame and the veneer are shaped to fit well with the adjacent and opposed teeth in a patient's mouth.

In recent years ceramic materials have been widely used for making high-quality dental restorations because of their good physical, aesthetic and biological properties. In some applications such dental restorations are made by combining a ceramic framework and a ceramic veneer. The framework and the veneer may, for example, be ground or milled from a ceramic blank, or cast from a molten ceramic material. It is desirable that the dental restoration also has an appearance that matches or approximates the appearance of adjacent teeth.

The dental restoration is typically manufactured based on a physical and/or digital replication of the tooth to be restored and adjacent teeth. For example the relevant teeth may be captured physically by a dental impression and/or digitally by scanning the teeth, or a model obtained from the dental impression. A dentist typically provides such physical and/or digital replication to a dental technician who uses that replication to manufacture an appropriate dental restoration. The dental restoration may then be sent to the dentist for implantation in the patient's mouth.

The dental technician is typically provided with all information necessary to complete the dental restoration so that, once such information is obtained from the patient, the dental restoration can be manufactured independently from the patient. Therefore such information typically also includes information about the shape of the tooth prepared to receive the dental restoration, which can be used to finish the dental restoration including an interface for connecting the dental restoration with the prepared tooth.

For example U.S. Pat. No. 6,398,554 discloses a process for the production of a dental prosthesis having a cap for fitting on a human tooth and a crown supported by the cap. The process comprises: taking a digitized three-dimensional image of the tooth; based on the tooth image, defining a digitized internal surface of the prosthesis corresponding to an inner surface of the cap; defining a digitized external surface of the prosthesis, on the basis of environmental parameters of the prosthesis, and taking into account of constraints from the internal surface of the prosthesis; and by use of the internal and external surfaces of the prosthesis, defining an external surface of the cap to form a digitized model of the cap.

US-A-2006/0257824 discloses a method of producing a prosthesis made of a framework as a first component, and a veneer as a second component. The first and second components can be designed by use a CAD system accounting for internal and external surfaces of the prosthesis.

EP application no. 07108206.9 relates to a method of making a veneer for a dental restoration comprising a frame and the veneer. The veneer can be obtained from a veneer precursor made of an open-celled material. An exterior surface of the veneer precursor may be formed based on a virtual model of an exterior surface of the dental restoration. An interior surface of the veneer precursor may be formed based on a virtual model of an exterior surface of a frame. The exterior surface of the dental restoration may be designed on a CAD system by use of surface data obtained from scanning a patient's tooth, scanning a temporary restoration, or scanning a model of a patient's tooth.

There is still a need for a method which provides an efficient workflow for restoring a tooth by use of a separately manufactured dental restoration. It is particularly desirable to minimize and/or efficiently control interactions between the patient, the dentist and the dental technician. A workflow for restoring a tooth should be preferably convenient for the patient. Further such workflow should be time saving and easy to handle for the dentist and the dental technician. It is also desirable to provide a method which provides a precise and optically pleasant dental restoration. Moreover an overall workflow of restoring a tooth and therefore a method of making a dental restoration is preferably relatively inexpensive.

SUMMARY OF THE INVENTION

In a first aspect the invention relates to a method of making a dental restoration from a frame and a veneer. The frame and the veneer each have an inner and an outer surface, wherein the inner frame surface corresponds to an inner surface of the dental restoration and the outer veneer surface corresponds to an outer surface of the dental restoration. The inner veneer surface and the outer frame surface are adapted, for example shaped, to be mated with one another to form the dental restoration.

The method comprises the steps of:
(a) providing an outer veneer surface in the form of surface data;
(b) determining an outer frame surface in the form of surface data, based on the outer veneer surface;
(c) providing an inner veneer surface in the form of surface data, based on the outer frame surface; and
(d) providing an inner frame surface in the form of surface data, based on a natural tooth surface prepared to receive the dental restoration;

The term "surface data" within the scope of this specification relates to data that are adequate to represent a three-dimensional surface. Such surface data may be used in a dental CAD system for designing the dental restoration.

For better understanding only, this specification generally refers to "the tooth" to be restored although the scope of the invention encompasses more than one tooth.

The invention is advantageous in that it may allow for designing at least part of a dental restoration independently from a preparation of a tooth to be restored. The invention may further allow for splitting up the design of the outer and inner shapes of the dental restoration. For example at least part of the exterior shape of the dental restoration may be designed without the availability of the inner shape of the dental restoration that forms the interface to the natural tooth. As an advantage the dental restoration may be at least partially prepared in parallel to the preparation of a patient's tooth. Consequently the time period required for restoration of a patient's tooth may be minimized. A patient may for example need to visit the dentist only a few times, or even once, to obtain a dental restoration of the type described herein. In this way also a temporary restoration of a patient's tooth may be saved, or a temporary restoration having a reduced durability may be sufficient.

As another advantage the shape of the frame may be designed according to an optimized shape of the veneer. For example the frame may be shaped according to minimum and maximum thicknesses of the veneer. Thereby undesirably thin and thick areas in the veneer, and therefore the risk for chipping, may be reduced.

In one embodiment the steps (a) to (d) of the method of the invention are performed in the order (a), (b), (c), and (d).

The prepared natural tooth surface of step (d) may be scan data obtained from scanning the natural tooth to be restored, or a replication of that tooth. A replication may be a negative or positive (physical) model of the tooth. A negative model may be a dental impression, and a positive model may be a plaster model casted from such dental impression, for example. The scan data may be loaded in the CAD system via network or a data carrier, and may be stored on the system for further use.

In step (b) of the method of the invention the outer frame surface may be determined based on the outer veneer surface independent from the inner frame surface. For example the outer frame surface may be determined without the availability or use of the inner frame surface. Thus the shape of the inner frame surface may not be required for this step, as well as the shape of the prepared natural tooth. This may allow the outer frame surface to be determined even at a stage the tooth to be restored is still unprepared.

In step (c) the inner veneer surface may also be determined based on the outer veneer surface. This may be advantageous for designing the veneer according to a minimum and/or a maximum thickness, for example to achieve certain optical and/or stability characteristics. Thus a veneer may be provided with a pleasant appearance, and chipping of the veneer may be prevented.

In one embodiment the method of the invention comprises the step of shaping the outer frame surface and/or the step of shaping the inner veneer surface to account for at least one intermediate layer arranged between the frame and the veneer. The step(s) of shaping the inner veneer surface and/or the outer frame surface is preferably performed using computer-aided design (CAD). The outer frame surface and the inner veneer surface may particularly shaped, such that in the final (physical) dental restoration a space for the intermediate layer is provided. The intermediate layer in the final dental restoration may be a bonding layer interconnecting the frame and the veneer. Such an intermediate layer may further comprise colorants to provide the dental restoration with a certain color, or to trim the color(s) of the veneer and/or the frame toward another color. More than one intermediate layers are possible, for example differently colored layers. The intermediate layer(s) may thus provide for a good durability and a pleasant optical appearance of the dental restoration.

In another embodiment the method of the invention, comprises the step of providing the veneer with an inner surface that is proportionally scaled relative to the outer frame surface. Further the method may comprise the step of providing the frame with an outer surface that is proportionally scaled relative to the inner veneer surface. Thus the inner veneer surface and the outer frame surface may be proportionally scaled with respect to one another. Therefore the intermediate layer may have a generally uniform thickness. This may provide for a uniform color of the final dental restoration.

The term "proportionally scaled" within the context of this specification means that each of the three dimensions of a scaled object is enlarged or reduced relative to the corresponding dimension of the original object by preferably substantially the same magnification or reduction factor. Further, "proportionally scaled" may include tolerances of the magnification or reduction factor in each dimension so that each of the three dimensions of the scaled object may be scaled relative to the corresponding dimension of the original object by three individual factors being different from each other by 1% to 5%. Instead proportionally scaling a surface may also be generated from an offset of another surface. For example the inner veneer surface may be obtained from an offset of the outer frame surface, or vice versa.

In one embodiment the method of the invention, comprises the step of shaping the inner frame surface to account for at least one fixation layer for connecting the frame and the prepared natural tooth. Thereby the frame may be adapted for mating with the prepared natural tooth surface with the fixation layer arranged between. The step of shaping the inner frame surface is preferably performed using computer-aided design (CAD). The fixation layer of the final dental restoration may be adapted for securing the frame (or the dental restoration) on the natural tooth. A material as it may be used for providing a fixation layer is for example RelyX™ Unicem, as available from 3M ESPE AG, Germany.

The method of the invention may further comprise the step of providing the frame with an inner surface that is proportionally scaled relative to the prepared natural tooth surface. Therefore the fixation layer may obtain a generally uniform thickness. This may provide good durability of the bond between the frame (or the dental restoration) and the natural tooth. The method of the invention however may also comprise the step of providing the frame with an offset of the outer surface of the prepared natural tooth.

In one embodiment of the invention step (a) comprises the steps of:

(aa) providing a predefined standard tooth surface in the form of surface data;

(ab) providing an option to manually modify the standard tooth surface; and (ac) accepting the standard tooth surface or modified standard tooth surface to provide the outer veneer surface in the form of surface data.

The predefined standard tooth surface may be provided by a database holding a plurality of standard tooth surfaces. Such standard tooth surfaces may be scaled and/or reshaped according to conditions and/or limitations resulting from teeth that surround the tooth to be restored. For example, a standard tooth surface may be obtained from the database and resized to fit with teeth that surround the tooth to be restored.

Further the standard tooth surface may be locally deformed to avoid collisions with such surrounding teeth. Thus the outer veneer surface may be determined automatically to a relatively large extent, and manually adapted further. Therefore efforts for manual adaptations may be reduced.

The option to manually modify the standard tooth surface may comprise features for changing the position, the shape and/or the orientation of the standard tooth surface. Examples of such features are dragging, stretching, compressing, rotating, of the standard tooth surface or portions of it. The option to manually modify the standard tooth surface is preferably software implemented and provided on the CAD system. Preferably the predefined standard tooth surface, in the initial and in modified stages, is displayed by the CAD system. Further the tooth to be restored, and optionally the surrounding teeth, may be displayed on the system. Thus a user may modify the predefined standard tooth surface to match the tooth to be restored as well as the surrounding teeth by aid of the display of the CAD system.

The CAD system may provide a feature allowing the user to accept the initial or modified standard tooth surface as the outer veneer surface (or the outer surface of the dental restoration), for example, when the user is satisfied with the shape of the tooth surface.

In another embodiment of the invention the method, comprises the step of scanning of the natural tooth (or a replication of the tooth) to provide the prepared natural tooth surface in the form of surface data. The method may further comprise the step of scanning surrounding teeth to provide ancillary data. Such ancillary data may be used as reference in the design of the dental restoration.

In another embodiment of the invention the method comprises the step of automatically detecting a preparation margin of the prepared tooth. The method may further comprise the step of providing an option to manually modify the detected preparation margin. The preparation margin, typically representing an important limitation in the design of the dental restoration, thus may be determined mainly automatically, and adapted manually after. Therefore the determination of preparation margin may be performed relatively rapidly, and further relatively precisely.

In another embodiment of the invention the method comprises the step of evaluating a possible direction of assembly of the frame onto the prepared natural tooth, and determination of an assembly axis A aligned with that direction. In a further embodiment of the invention the method comprises the step of evaluating a possible direction of assembly of the veneer onto the frame, and determination of an assembly axis B aligned with that direction. This may allow for optimization of the wall thicknesses of the frame and the veneer, for example, because cutaways at the frame and/or the veneer that may be needed to avoid collisions during assembly of the veneer and the frame may be minimized.

In one embodiment of the invention the method comprises the step of selecting the predefined standard tooth surface from the database, based on at least one of the preparation margin, the ancillary data, and user inputs. For example a user may input a tooth position relative to other teeth in a patient's mouth in a CAD system, and the CAD system may automatically select a suitable standard tooth surface from the database. The CAD system may further use the preparation margin and/or the ancillary data for this selection. Thus a standard tooth surface may be provided which largely matches the desired shape of the dental restoration. This may save a user time in the design of the dental restoration.

In another embodiment of the invention the method comprises the step of providing an option to enter a thickness of an intermediate layer between the veneer and the frame. In a further embodiment of the invention the method comprises the step of providing an option to enter a fixation layer between the frame and the prepared natural tooth. For example a user may input the intermediate layer thickness and/or the fixation layer thickness into the CAD system, and the system may automatically calculate the frame and veneer surfaces appropriately. This may provide a rapid and precise design of the dental restoration.

In a further embodiment of the invention the method comprises the step of performing a collision analysis for an assembly of the frame onto the natural tooth along the assembly axis A. In another embodiment of the invention the method comprises the step of performing a collision analysis for an assembly of the veneer onto the frame along the assembly axis B. The result of the collision analyses may be used to remove portions from the frame and/or veneer which potentially collide when the frame and the veneer are assembled. Thus it may be ensured that the veneer and the frame can be assembled as well as the frame can be assembled on the prepared tooth without damaging the veneer and/or the frame. Costs for modifications of the dental restoration, or for manufacturing a new dental restoration may therefore also be avoided. The collision analyses for the assembly of the frame onto the natural tooth or for the assembly of the frame and the veneer may also be based on precursors of the frame and/or the veneer. In particular the collision analysis may be based on the assembly of the frame and a veneer precursor, latter being scaled (for example enlarged) relative to the final veneer.

In another embodiment of the invention the method comprises the step of scaling the inner and outer frame surfaces, and at least the outer veneer surface. This may be useful to account for a change in size that may occur during the manufacturing of the frame and/or the veneer. For example the frame and/or the veneer may be shaped (for example machined) from a pre-sintered material which is sintered finally and thereby shrinks. To account for such shrinkage the frame and/or veneer may be (proportionally) enlarged, so the frame and/or the veneer obtain(s) their final shape during sintering.

In one embodiment the method of the invention comprises the step of machining a frame precursor. Further the method of the invention may comprise the step of machining a veneer precursor. The frame precursor and the veneer precursor may be proportionally scaled relative to the frame and the veneer. The method of the invention may comprise the step of sintering of the frame precursor to provide a frame. Sintering may cause the frame precursor to shrink, so that the frame obtains its final size. In a preferred embodiment the method further comprises the steps of providing a slurry comprising a glass ceramic material, and combining the veneer precursor and the frame with the slurry in between. Thereby a dental restoration precursor may be provided. The method of the invention further preferably comprises the step of sintering the dental restoration precursor to provide the dental restoration. During this step also the veneer may shrink and thereby obtain its final size.

A frame or frame precursor may be made of a ceramic material. For example, one comprising between 90% and 99% by weight zirconium oxide, and preferably between 91% and 97.25% by weight zirconium oxide. The ceramic material of the frame may further comprise 0% to 1% by weight aluminium oxide. The ceramic material may also be based on aluminium oxide, in which case it may comprise 90% to 99% by weight aluminium oxide and 0% to 1% by weight zirconium oxide. Further the ceramic material may generally comprise 0% to 10% by weight of at least one of hafnium oxide, yttrium oxide and oxides from gallium, germanium, and indium. The ceramic material may also comprise 0.0005% to 1.5% by weight of coloring additives, selected from the group consisting of the oxides $Fe_2O_3$, $Er_2O_3$ and/or $MnO_2$. The ceramic material is preferably selected to be compatible for use in human bodies A frame or frame precursor may further be made of metal. Such a metallic frame may, for example, be manufactured by the "lost wax" method which is known to the person skilled in the art. Thus, the metallic frame may be casted from metal or a metal alloy, or may be machined from a blank of metal or metal alloy.

The metallic frame may be characterized by at least one of the following features:

The coefficient of thermal expansion of the metal the metallic frame is made of may range from about $9.6*10^{-6}K^{-1}$ to about $17.3*10^{-6}K^{-1}$. Other suitable ranges include from about $9.6*10^{-6}K^{-1}$ to about $15.2*10^{-6}K^{-1}$ and $13.8*10^{-6}K^{-1}$ to about $15.2*10^{-6}K^{-1}$ and $16*10^{-6}K^{-1}$ to about $17.3*10^{-6}K^{-1}$.

The metallic frame may comprise metals selected from the group consisting of Ti, Au, Pt, Pd, Ag, Zn, Co, Cr, Mo, W, Ni and combinations and alloys thereof.

The metallic frame may be comprised of or may consist of a pure metal only or of a metal alloy. Commercially available metal alloys which were found to be useful for the present invention include for example those described in Table 1 below.

TABLE 1

| Supplier | Alloys with high fraction of noble metals | Alloys with reduced fraction of noble metals | Titanium | Palladium based alloys | Non-precious alloys |
|---|---|---|---|---|---|
| Argen | Argedent 90 | Argedent Euro | | Argelite 61 | Argeloy N.P. Special |
| Wieland | Porta ™ PK | Porta ™ SMK | | Simidur ™ S2 | |
| Bego | PontoStar H | BegoCer G | | BegoPal | Wirobond ™ 280 |
| Dentaurum | Triloy | | rematitan ® M | | Remanium ® CS |
| DeguDent ™ | Degudent ™ G | Degudor ™ | | | |

A veneer or veneer precursor may be made of a glass ceramic material. An exemplary formulation of a glass ceramic as it may be used with the present invention comprises 60% to 70% by weight of silica, 9% to 13% by weight of alumina, 5% to 10% by weight of potassium-oxide, 9% to 13% by weight of sodium-oxide, 0% to 1% by weight of lithium-oxide, 2% to 5% by weight of calcia, 1% to 2% by weight of barium-oxide, 0% to 1% by weight of zirconium oxide and 0% to 1% cerium-oxide or cerium-fluoride.

The frame precursor may be made of a pre-sintered ceramic material, and the veneer precursor may be made of a pre-sintered glass-ceramic material. Further the frame may be made of a sintered ceramic material, and the veneer precursor may be made of a sintered material. The sintered material referred to in this specification preferably has a material density in a range of 2 $g/cm^3$ to 2.7 $g/cm^3$, and the pre-sintered material preferably has a material density in a range of 30% to 92% of the material density of the sintered material. Preferably the material density of the pre-sintered material is in a range of 40% to 60% of the material density of the sintered material, and more preferably in a range of 45% to 55%.

The frame and/or the veneer may however also be obtained by first providing a wax model, using the wax model to make a mold, and using the mold to cast the frame and/or the veneer. Instead of wax other suitable materials may be used, including materials allowing the model to be made by rapid prototyping.

In particular, the veneer referred to in this specification preferably has a material density in a range of 2 $g/cm^3$ to 2.7 $g/cm^3$, and the veneer precursor preferably has a material density in a range of 30% to 92% of the material density of the veneer. Preferably the material density of the veneer precursor is in a range of 40% to 60% of the material density of the veneer, and more preferably in a range of 45% to 55%.

For example, the material density of the veneer precursor (or the pre-sintered material) may be in a range of 0.6 $g/cm^3$ to 1.84 $g/cm^3$ and the veneer (or the sintered material) obtained from it may have a material density of about 2 $g/cm^3$. In another example the material density of the veneer precursor (or the pre-sintered material) may be in a range of 0.81 $g/cm^3$ to 2.5 $g/cm^3$ and the veneer (or the sintered material) obtained from it may have a material density of about 2.7 $g/cm^3$. The veneer precursor (or the pre-sintered material) may generally have a material density in a range of 0.6 $g/cm^3$ to 2.5 $g/cm^3$.

Typically the difference between the density of the veneer precursor and the density of the veneer (or the pre-sintered material and the sintered material, respectively) is a result of the presence of a higher amount of cells within the veneer precursor (or the pre-sintered material) than in the veneer (the sintered material).

The average size of the particles forming the pre-sintered material as referred to in this specification is typically in a range of about 10 μm to about 60 μm, and preferably about 30 μm. The distribution of the particle size may be for example:
  10% of the particles smaller than about 3 μm;
  50% of the particles smaller than about 26 μm; and
  90% of the particles smaller than about 71 μm.

In more particular the average particle size which the pre-sintered material referred to in this specification is comprised of may be about 20 μm, for example according to a particle size distribution in which:
  10% of the particles are smaller than about 1.2 μm;
  50% of the particles are smaller than about 10 μm; and
  90% of the particles are smaller than about 45 μm.

The volume of the cells in the pre-sintered material relative to the total volume of the pre-sintered material as referred to in this specification is typically in a range of about 20% to about 40%, and more preferably in a range of about 30% to about 38%.

The slurry may comprise a powdery glass ceramic material, for example of the type used for the veneer or veneer precursor. The slurry may further comprise water, and optionally colorants.

A second aspect of the invention is directed to a computer system configured to perform the method of the invention. The computer system may comprise or be connectable to a database holding a plurality of standard tooth surfaces. The computer system further may be connectable to a scanner for scanning teeth in a patient's mouth (intra-oral scanner), or to a scanner for scanning a replication of a patient's teeth. Further, the computer system may be connectable to a machine for machining dental parts, particularly to a milling and/or grinding machine for machining a frame and/or a veneer and/or precursors thereof. Further a rapid prototyping machine may be used. The computer system may comprise a remote connectivity with at least one of the scanner, the machine and the database. In this regard a remote connection may be, for example, comprise an Internet-based connection. The computer system of the invention may therefore provide for performing one or more of the method steps of the invention in parallel, and thus contribute and/or enable for the advantages of the invention.

DETAILED DESCRIPTION OF THE FIGURES

The following Figures illustrate an exemplary workflow according to an embodiment of the method of the invention. The workflow is preferably performed on a computer system, unless indicated otherwise.

Figure 1:
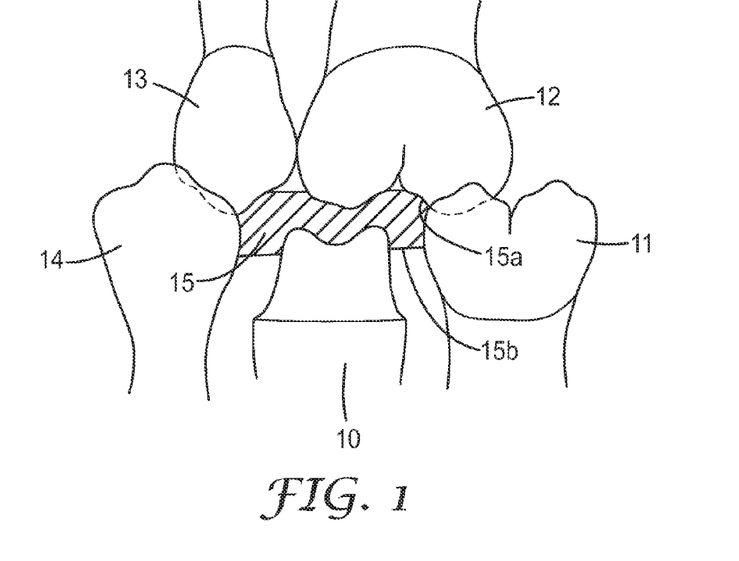
FIG. 1 is an image of some of a patient's teeth according to an embodiment of the invention.

FIG. 1 schematically shows an image of some of a patient's teeth as it may be shown on a computer screen of a computer system. A tooth 10 prepared to receive a dental restoration is shown together with adjacent teeth 11, 12, 13, 14. The image in this example may be based on scan data which are stored in the computer system. Such scan data may be obtained from intra-orally scanning a patient's teeth, or from scanning a replication (for example a plaster model, or a dental impression) thereof. The scan data in the example comprises the outer surface of the tooth 10 in the form of surface data. The scan may further comprise the outer surfaces of the teeth 11, 12, 13, 14 (that are located next to the tooth 10) in the form of surface data. FIG. 1 further shows a bite registration 15 which captures the positional relationship between opposing teeth. The bite registration may be obtained from a wax impression which is typically made by having a patient biting on a thin piece of wax. The bite registration thus has surfaces 15a, 15b reproducing at least portions of the occlusion surfaces of the teeth 10, 11, 12, 13, 14. A so-formed bite registration may subsequently be scanned to provide bite registration surfaces 15a, 15b in the form of surface data. However the bite registration may also be obtained from an intra-oral scan of the patient's teeth, for example, in which case bite registration surfaces 15a, 15b may be obtained directly in the form of surface data. The tooth surfaces and/or the bite registration surfaces 15a, 15b may form ancillary data defining the available space for the dental restoration.

In the example shown the tooth 10 is already prepared to receive the dental restoration, however, in other embodiments the tooth to be restored at this stage may still be unprepared or only partially prepared. A partial preparation may essentially only include a determination of the preparation margin (transition between prepared tooth structure and natural tooth structure). Therefore at the stage of capturing the patient's teeth a patient may not need to be treated with anesthesia. Further, a temporary restoration for protecting the prepared tooth may not be necessary.

Figure 2:
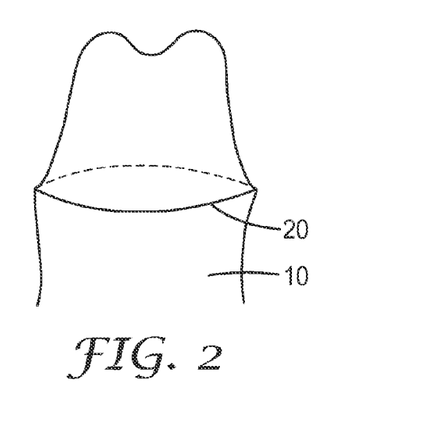
FIG. 2 is a detail image of an a tooth prepared to receive a dental restoration according to an embodiment of the invention.

FIG. 2 shows in detail the image of the tooth 10 which is already prepared to receive a dental restoration and therefore has a preparation margin 20. The computer system preferably comprises software which is adapted to detect the preparation margin based on the scan data stored in the system. Preferably the detected preparation margin is indicated on the computer screen, and a user is given the opportunity to modify the margin as desired. Thereby a relatively precise determination of the preparation margin may be achieved.

Figure 3:
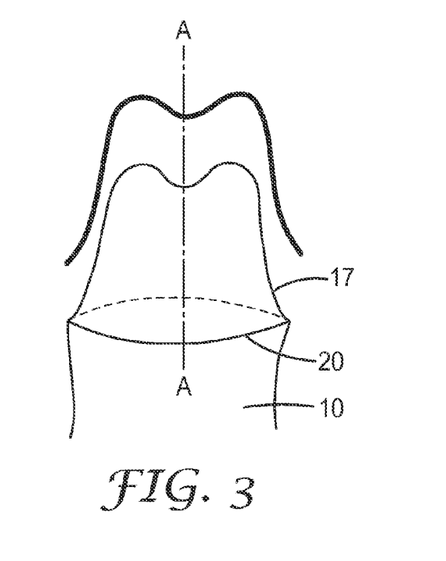
FIG. 3 is an image illustrating the determination of an assembly axis A according to an embodiment of the invention.

FIG. 3 shows the image of the tooth 10 and a virtual surface 16 generally corresponding to the shape of the prepared surface 17 of the tooth 10. The software is further preferably adapted to determine an assembly axis A that represents a direction along which the virtual surface 16 may preferably be moved towards prepared surface 17 for mating. The assembly axis is preferably determined so that collisions between surfaces 16 and 17 during assembly are minimized. The assembly axis is preferably used for the design of an inner surface of the dental restoration, for example, to ensure that the finished dental restoration can be easily fitted with the tooth to be restored.

Figure 4:
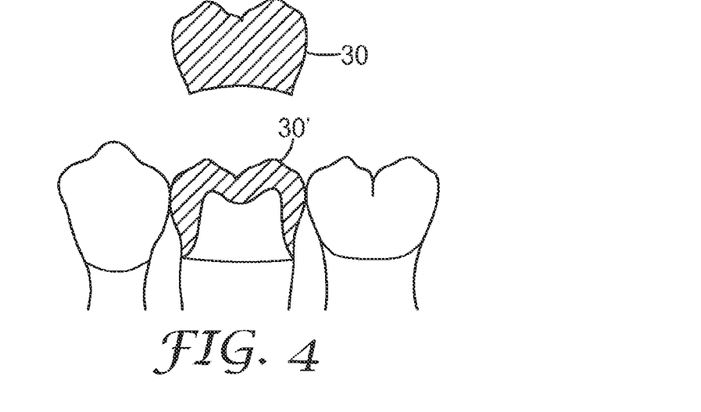
FIG. 4 is an image illustrating a standard tooth selected from a database according to an embodiment of the invention.

FIG. 4 shows a standard tooth surface 30 obtained from a database that preferably holds a plurality of standard tooth surfaces. The software may automatically select a certain standard tooth surface from the database based on a user input (position of tooth, for example) and/or based on the scan data. The software preferably adapts the outer tooth surface 30 to the particular situation in a patient's mouth. In this case the software preferably reshapes outer tooth surface 30 at least according to the restrictions given by the bite registration surfaces 15a, 15b (FIG. 1). The software preferably also scales the tooth surface according to the situation captured by the scan data. Thus a preliminary outer tooth surface 30' is obtained representing a preliminary outer surface of the dental restoration.

Figure 5A:
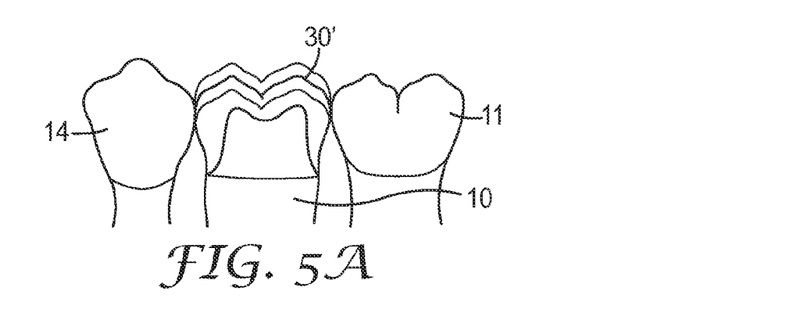
FIG. 5A, 5B, 5C are images illustrating positional and dimensional modifications of the standard tooth according to an embodiment of the invention.
Figure 5B:
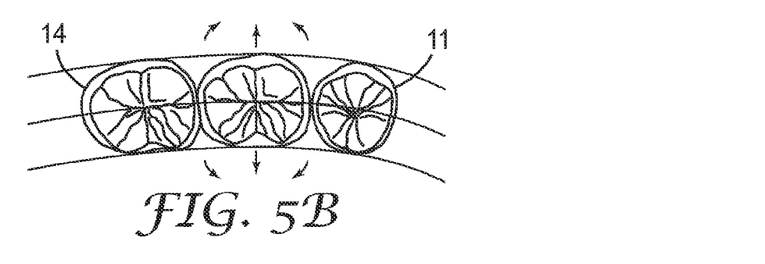
Figure 5C:
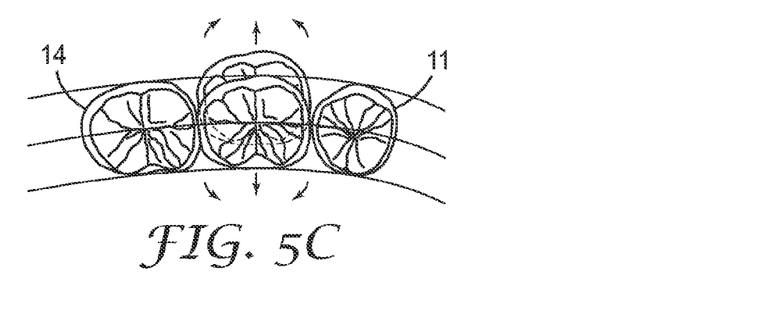

FIGS. 5A, 5B and 5C illustrate a manual adjustment of the previously automatically determined preliminary outer surface 30'. The outer surface 30' is (virtually) placed over the tooth 10, which is located between adjacent teeth 14, and 11. The software may therefore be adapted for allowing a user to resize, deform, incline and/or move the preliminary outer surface 30' as desired to arrive at a final outer surface of the dental restoration. However the software may also allow a user to accept the automatically determined preliminary outer surface 30' as the final outer surface 30" (shown in FIG. 7) of the dental restoration. For this step the presence of the prepared surface 17 (shown in FIG. 3) is optional. The steps shown in FIGS. 2 and 3 may therefore be performed at a later stage (after the steps illustrated in FIGS. 4, 5A, 5B, 5C). Therefore the design of the outer surface of the dental restoration may be finished independently from the preparation of the tooth to be restored. Consequently the tooth to be restored may be prepared in parallel to (or after) the design of the outer surface of the dental restoration. Thus, time may be saved in the manufacture of the dental restoration.

Figure 6:
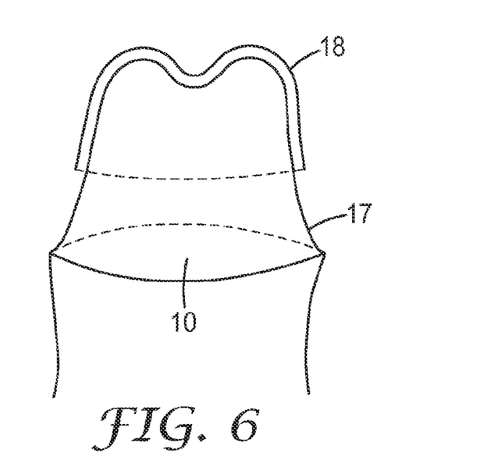
FIG. 6 is an image illustrating the determination of an inner surface of the dental restoration according to an embodiment of the invention.

FIG. 6 illustrates the determination of the inner surface of the dental restoration. The steps shown in FIGS. 2 and 3 may be performed just before. The inner surface 18 of the dental restoration may correspond to a proportional magnification of prepared surface 17. Therefore a gap for receiving a bonding material (for example cement) between the dental restoration and the tooth 10 may be created. The software may allow a user to select or input the desired thickness of the gap.

Figure 7:
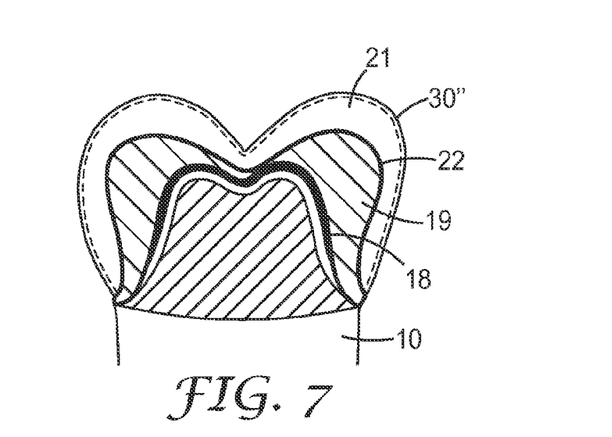
FIG. 7 is an image illustrating the determination of an outer frame surface according to an embodiment of the invention.

FIG. 7 illustrates the splitting of the dental restoration in a frame 19 and a veneer 21. The dental restoration is shown positioned on the tooth 10. The software preferably uses the final outer surface 30" to generate an outer frame surface 22. To generate the outer frame surface 22 parameters like for example a minimum or maximum wall thickness of the veneer 21 and/or the frame 19 may be used. After this step the final outer surface 30", the outer frame surface 22, and the inner surface 18 of the dental restoration may be determined. The determination of the outer frame surface 22 based on outer surface 30" is advantageous in that it helps to provide a good mechanical support of the veneer by the frame. For example, critically thick or thin portions of the veneer may be avoided. Therefore the veneer of the dental restoration may be prevented from chipping.

Figure 8:
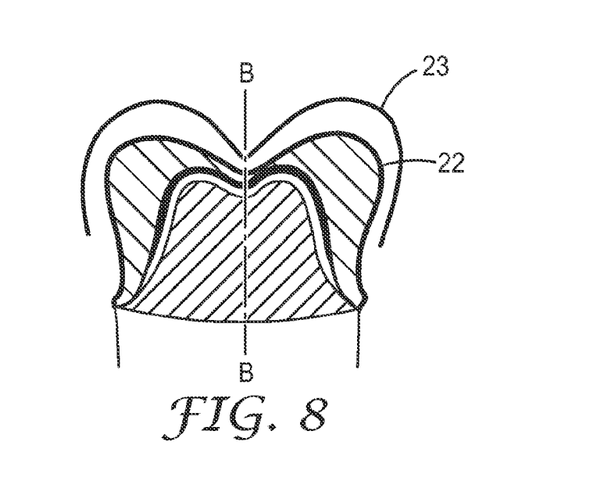
FIG. 8 is an image illustrating the determination of an assembly axis B according to an embodiment of the invention.

FIG. 8 illustrates the determination of an assembly axis B. The procedure corresponds generally to the procedure described for FIG. 3. An imaginary digital surface 23 is shown which generally corresponds to the outer frame surface 22. The assembly axis B is preferably used for the design of an inner veneer surface to allow the veneer to be easily fitted with the frame.

Figure 9:
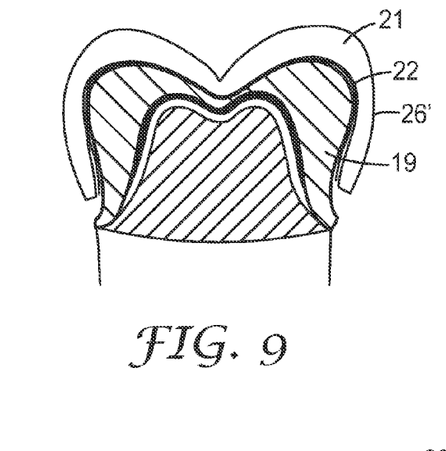
FIG. 9 is an image illustrating the determination of an inner veneer surface according to an embodiment of the invention.

FIG. 9 shows a computer simulation of the frame 19 and the veneer 21 when mated. The software on the computer system calculates based on the outer frame surface 22 an inner veneer surface 26'. The inner veneer surface 26' may also be calculated based on the outer surface 30" (shown in FIG. 7) of the dental restoration. The inner veneer surface 26' is determined so that a gap is left between the inner veneer surface 26' and the outer frame surface 22. This gap may account for a bonding material placed between the frame and the veneer in the final (physical) dental restoration. In the example the inner veneer surface 26' is essentially a proportional magnification of the outer frame surface 22.

Figure 10:
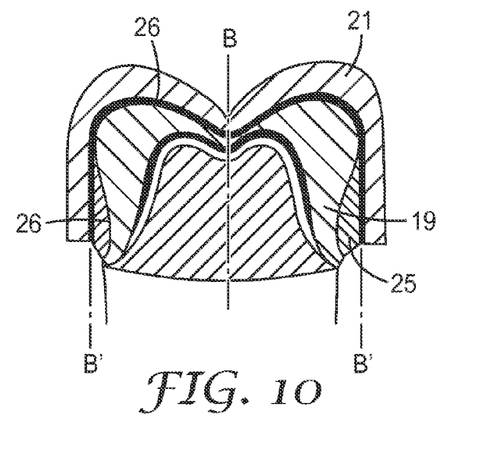
FIG. 10 is an image illustrating the removal of undercuts at the inner veneer surface.

As shown in FIG. 10 the frame 19 has undercuts 25, 26 which would make an assembly of the veneer 21 and the frame 19 impossible. The software is preferably adapted to eliminate such undercuts by cutting away areas of the veneer (and/or the frame) which possibly collide with the frame. In the example shown such cutaways extend along axes B' which are parallel axes of assembly axis B.

Figure 11:
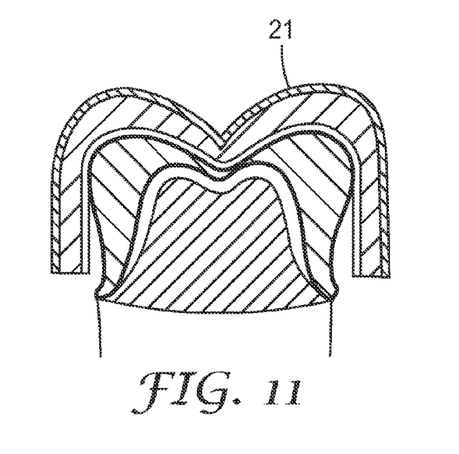
FIG. 11 is an image illustrating a proportional magnification of the veneer according to an embodiment of the invention.
Figure 12:
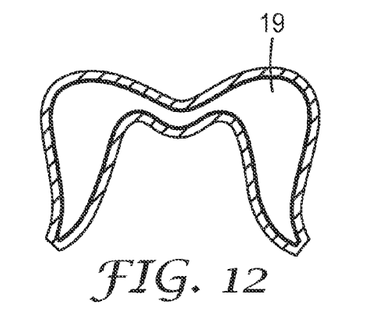
FIG. 12 is an image illustrating a proportional magnification of the frame according to an embodiment of the invention.

FIGS. 11 and 12 illustrate a proportional magnification of the veneer 21 (FIG. 11) and the frame 19 (FIG. 12) to account for a shrinkage of the parts during sintering. Based on the magnified surfaces machining data may be automatically generated. The machining data may be used to machine a (magnified) frame precursor and a (magnified) veneer precursor that are oversized with respect to the sintered frame and/or veneer.

The frame precursor may be sintered to obtain the frame. The veneer precursor and the (sintered) frame may be assembled with an intermediate layer disposed in between so that a dental restoration precursor is formed. The dental restoration precursor may then be sintered to obtain the final dental restoration.

Figure 13:
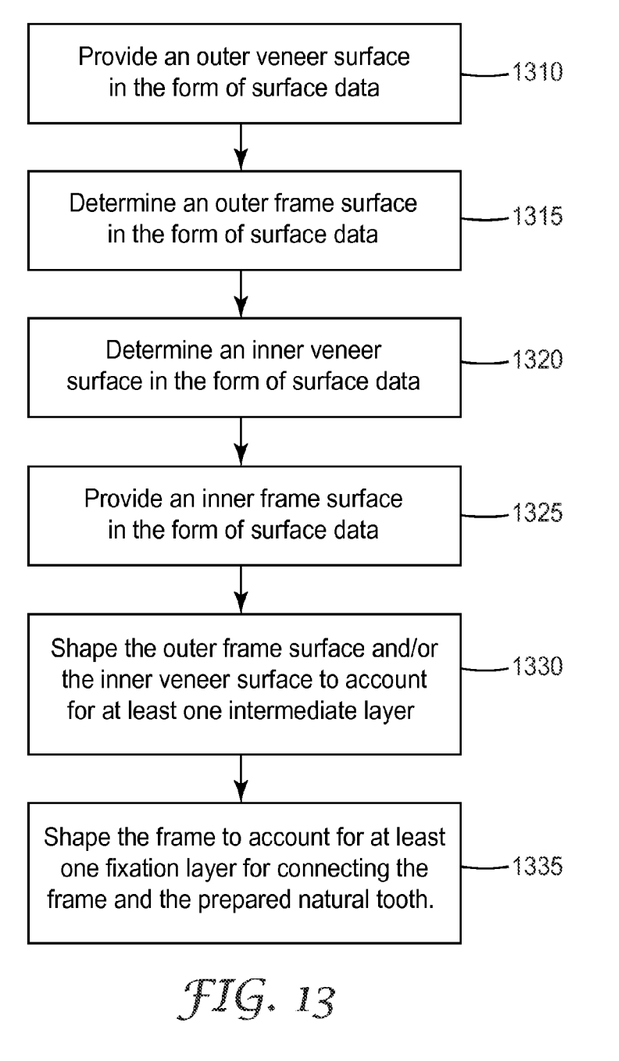
FIG. 13 is a functional flow diagram of one embodiment of a system of making a dental restoration from a frame and a veneer, which includes example steps of the system.

FIG. 13 illustrates a functional flow diagram of one embodiment of a system of making a dental restoration from a frame and a veneer, which includes example steps of the system. The frame and the veneer have inner and outer surfaces, where the inner frame surface corresponds to an inner surface of the dental restoration and the outer veneer surface corresponds to an outer surface of the dental restoration, with the inner veneer surface and the outer frame surface being adapted to be mated with one another to form the dental restoration. First, the system provides an outer veneer surface in the form of surface data (step 1310). Next, the system determines an outer frame surface in the form of surface data, based on the outer veneer surface (step 1315); and determines an inner veneer surface in the form of surface data, based on the outer frame surface (step 1320). The system provides an inner frame surface in the form of surface data, based on a natural tooth surface prepared to receive the dental restoration (step 1325). The system can further shape the outer frame surface and/or the inner veneer surface to account for at least one intermediate layer arranged between the frame and the veneer (step 1330). The system alternatively may shape the frame to account for at least one fixation layer for connecting the frame and the prepared natural tooth (step 1335). The system may further perform at least one of the steps of: scanning of the natural tooth prepared to receive the dental restoration, and optionally surrounding teeth to provide ancillary data; automatically detecting a preparation margin of the prepared tooth, and providing an option to manually modify the detected preparation margin; selecting a predefined standard tooth surface from a database based on at least one of the preparation margin, the ancillary data, and user inputs; evaluating a possible direction of assembly of the frame onto the prepared natural tooth, and determination of an assembly axis A aligned with that direction; evaluating a possible direction of assembly of the veneer and the frame, and determination of an assembly axis B aligned with that direction; performing a collision analysis for an assembly of the frame onto the natural tooth along the assembly axis A, and removing colliding portions from the frame; performing a collision analysis along an assembly of the veneer (a veneer precursor) and the frame (or a frame precursor) along the assembly axis B, and removing colliding portions from the veneer (precursor) and/or the frame (precursor); providing an option to enter a thickness of an intermediate layer between the veneer and the frame; providing an option to enter a fixation layer between the frame and the prepared natural tooth; and scaling the inner and outer frame surface, and the outer veneer surface.

The invention has now been described by way of several examples. However, people of ordinary skill in the art will understand that various changes and substitutions can be made without departing from the scope of the invention.

The invention claimed is:

1. A method of making a dental restoration from a frame and a veneer, the frame and the veneer having inner and outer surfaces, wherein the inner frame surface corresponds to an inner surface of the dental restoration, and the outer veneer surface corresponds to an outer surface of the dental restoration, with the inner veneer surface and the outer frame surface being adapted to be mated with one another to form the dental restoration, the method implemented with a computer system with one or more processors and memories, the method comprising the steps of:
   (a) providing an outer veneer surface in the form of surface data;
   (b) determining, by the one or more processors, an outer frame surface in the form of surface data, based on the outer veneer surface;
   (c) determining, by the one or more processors, an inner veneer surface in the form of surface data, based on the outer frame surface; and
   (d) providing an inner frame surface in the form of surface data, based on a natural tooth surface prepared to receive the dental restoration.

2. The method of claim 1, comprising the step of shaping the outer frame surface and/or the step of shaping the inner veneer surface to account for at least one intermediate layer arranged between the frame and the veneer.

3. The method of claim 1, comprising the step of providing the veneer with an inner surface that is proportionally scaled relative to the outer frame surface.

4. The method of claim 1, comprising the step of shaping the frame to account for at least one fixation layer for connecting the frame and the prepared natural tooth.

5. The method of claim 1, comprising the step of providing the frame with an inner surface that is proportionally scaled relative to the prepared natural tooth surface.

6. The method of claim 1, wherein step (a) comprises the steps of:
   (aa) providing a predefined standard tooth surface in the form of surface data;
   (ab) providing an option to manually modify the standard tooth surface; and
   (ac) accepting the standard tooth surface or modified standard tooth surface to provide the outer veneer surface in the form of surface data.

7. The method of claim 1, comprising the step of machining a frame precursor.

8. The method of claim 7, comprising the steps of:
   sintering of the frame precursor to provide a frame;
   providing a slurry comprising a glass ceramic material, water, and optionally colorants;
   combining the veneer precursor and the frame with the slurry in between to provide a dental restoration precursor; and
   sintering the dental restoration precursor to provide the dental restoration.

9. The method claim 7, wherein the frame precursor is made from a pre-sintered ceramic material.

10. The method of claim 1, comprising the step of machining a veneer precursor.

11. The method of claim 10, wherein the veneer precursor is made from a pre-sintered glass-ceramic material.

* * * * *